United States Patent
Bruneau et al.

(10) Patent No.: US 6,503,261 B1
(45) Date of Patent: Jan. 7, 2003

(54) BI-DIRECTIONAL ATHERECTOMY BURR

(75) Inventors: Rodney J. Bruneau, Kirkland, WA (US); David H. Dillard, Redmond, WA (US); Gregory T. Lincicome, Bellevue, WA (US); Kristine Kaliszewski, Kent, WA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/765,126

(22) Filed: Jan. 17, 2001

(51) Int. Cl.[7] .............................................. A61B 17/22
(52) U.S. Cl. ...................... 606/159; 606/180; 606/170; 606/171; 604/22
(58) Field of Search ........................ 606/1, 108, 159, 606/170, 171, 180; 604/22

(56) References Cited

U.S. PATENT DOCUMENTS 4,445,509 A * 5/1984 Auth .......................... 606/159
5,849,023 A * 12/1998 Mericle ...................... 606/180
6,156,048 A * 12/2000 Wulfman et al. ........... 606/159

* cited by examiner

*Primary Examiner*—Jeanette Chapman
(74) *Attorney, Agent, or Firm*—Christensen O'Connor Johnson Kindness PLLC

(57) ABSTRACT

An atherectomy burr includes a number of cutting blades having a less aggressive cutting action when rotated in a first direction and a more aggressive cutting action when rotated in a second direction. In accordance with one embodiment of the invention, each cutting blade includes an abrasive surface that is substantially parallel to the outer surface of the cutting burr. Each blade further includes a second cutting surface that is substantially perpendicular to the outer surface of the burr. By selectively rotating the burr in either direction, a physician can cause the less aggressive or more aggressive cutting surface to engage deposits in a patient's vessel.

9 Claims, 1 Drawing Sheet

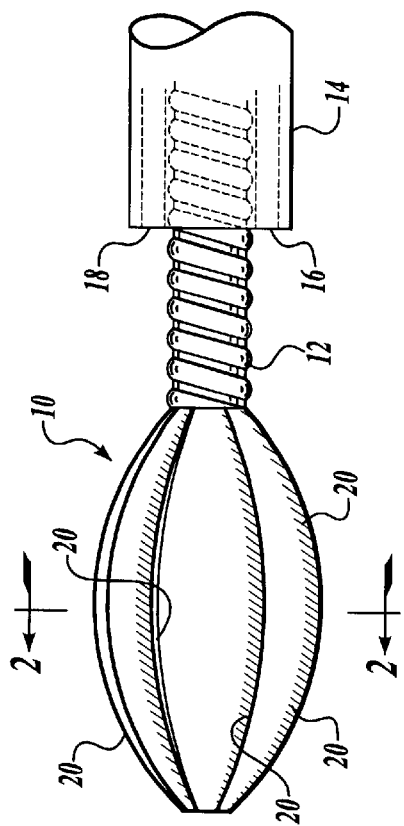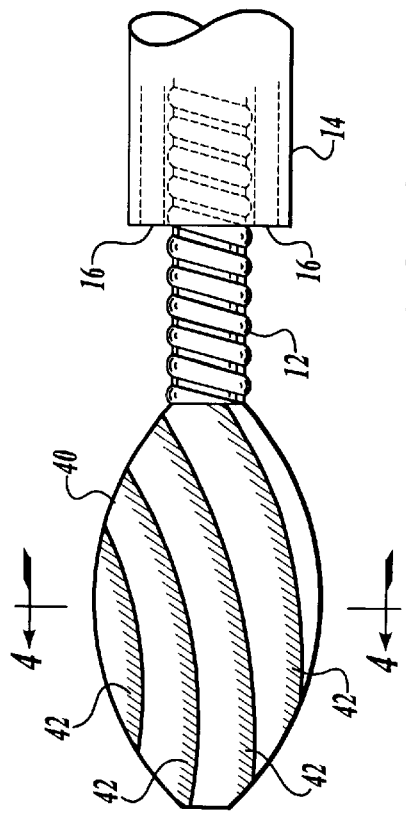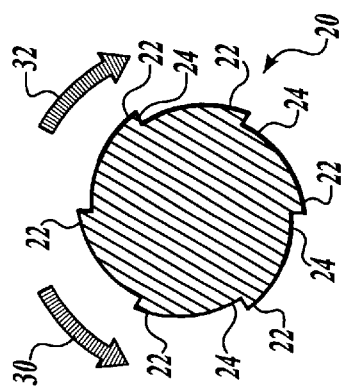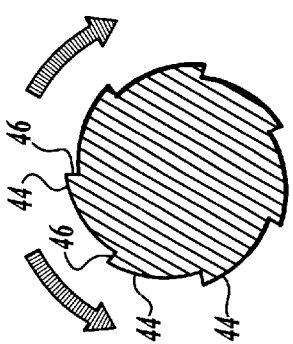

BI-DIRECTIONAL ATHERECTOMY BURR

FIELD OF THE INVENTION

The present invention relates to medical devices in general, and in particular to atherectomy devices for removing deposits from a vessel.

BACKGROUND OF THE INVENTION

Atherectomy burrs are becoming commonly used medical devices that remove deposits from a patient's vessel. A typical atherectomy device includes a driveshaft that is rotated by a gas turbine or electric motor and has an atherectomy burr disposed at its distal end. The atherectomy burr is typically an ellipsoidally shaped metal bead having an abrasive outer coating. The coating, which usually comprises a diamond grit, removes deposits from a vessel when the burr is rotated at high speed and advanced into the deposits or an occlusion.

While the use of an atherectomy device provides a minimally invasive technique for removing deposits from a vessel, there are some situations where the use of such devices has been avoided. For example, in saphenous vein grafts (SVGs), deposits tend to be loosely calcified and friable and can break up into large pieces before a high-speed atherectomy burr can disintegrate them. These lesions are also often covered with a fibrous cap, which is tough and flexible enough to resist disintegration by a high speed cutting burr. Therefore, these types of lesions often require ablation with a less differentially cutting low speed cutter. However, the anastomosis, or entry point, into the vein graft is often highly angulated and surrounded by scar tissue which is more suitable for removal with a more differentially cutting high speed cutting burr. Therefore, in order to perform an atherectomy procedure in an SVG, multiple cutting burrs must be employed, thereby adding to the expense and time required to perform the procedure.

In order to increase the number of locations in the body where a less invasive atherectomy procedure can be used to remove deposits from a vessel without the need to use multiple burrs, there is a need for an atherectomy device that can easily remove harder, more dense material in addition to softer, more friable occluding material such as that typically found in an SVG.

SUMMARY OF THE INVENTION

To address the above-mentioned shortcomings, the present invention is a bi-directional atherectomy device that includes a source of rotational motion and a driveshaft coupled to the source of rotational motion. An atherectomy burr at the distal end of the driveshaft has a number of cutting blades having a less aggressive cutting action when rotated in a first direction and a more aggressive cutting action when rotated in a second direction.

In one embodiment of the invention, the number of cutting blades have an abrasive surface that is substantially parallel to the outer surface of the burr and a cutting surface that is substantially perpendicular to the outer surface of the burr. When rotated in the first direction, the less aggressive, abrasive surface removes deposits from a vessel. When rotated in the second direction, the more aggressive, cutting surface removes deposits from the vessel.

In one embodiment of the invention, the one or more blades are parallel to the longitudinal axis of the burr. In another embodiment of the invention, the one or more cutting blades are spiraled along the length of the burr body.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 1 and 2 illustrate an atherectomy burr according to a first embodiment of the present invention; and FIGS. 3 and 4 illustrate an atherectomy burr according to another embodiment of the present invention.

DETAILED DESCRIPTION OF THE PREFERRED EMBODIMENT

FIG. 1 illustrates an atherectomy burr constructed in accordance with one embodiment of the present invention. The atherectomy burr 10 is secured to the distal end of a driveshaft 12 that is in turn rotated by a source of bi-directional rotation, such as a series of turbines or an electric motor (not shown). The driveshaft is routed through a guide catheter 14 that may include one or more additional lumens 16, 18. These additional lumens may be used to infuse liquids to an ablation site, or for aspirating debris removed from a vessel. In some instances, the driveshaft 12 and atherectomy burr 10 may include a central lumen such that the atherectomy burr and driveshaft can be routed over a conventional guide wire.

To allow the ablation burr 10 to remove various types of deposits from a patient's vessel, the ablation burr 10 includes a number of cutting blades 20 that have a less aggressive and more aggressive cutting surface. Each cutting blade 20 has a first edge 22 that is generally tangential to the outer surface of the ablation burr. Each cutting blade 20 also includes a second cutting edge 24 that is substantially perpendicular to the outer surface of the ablation burr. The first edges 22 are preferably covered with an abrasive material such as diamond chips, etc., that constitute a relatively less aggressive cutting surface. The transition between the first edge 22 and the second edge 24 forms a more aggressive cutting surface. When viewed in cross section as shown in FIG. 2, the burr has a ratchet configuration with each cutting blade 20 ramping radially outward to the point where the first edge 22 meets the second cutting edge 24 in a pattern that continues around the circumference of the burr.

When the atherectomy burr 10 is rotated in the direction of the arrow 30, the abrasive-covered edges 22 engage deposits or an occlusion within a blood vessel and ablate it. The particles removed from the blood vessel are sufficiently small such that they can be washed by blood flow downstream of the burr and dissipated by the body. When the ablation burr is rotated in the direction of the arrow 32, the second set of edges 24 engage the deposits or occluding material and remove it from a vessel. When the ablation burr 10 is rotated in the direction of the arrow 30, the second set of edges 24 are drawn over the tissue but do not engage it. Because the second set of edges 24 are more aggressive than the first set of edges 22, aspiration is usually provided through the catheter 14 in order to remove ablated material from the vessel.

Although the blades 20 are shown as extending along the length of the burr 10 in FIG. 1, it will be appreciated that the blades could extend less than the entire length of the burr. For example, it may be advisable to provide the burr with an atraumatic distal tip or proximal tail thereby requiring the length of the blades to be less than the entire length of the burr.

FIG. 3 illustrates an alternative embodiment of the atherectomy burr shown in FIG. 1. Here, an atherectomy burr 40 includes a number of cutting blades 42 that are spiraled along a length of the burr. As in the embodiments shown in FIGS. 1 and 2, each of the blades 42 includes a first abrasive edge 44 that is generally parallel to the outer surface of the burr and a second cutting edge 46 that is generally perpendicular to the outer surface of the burr. In operation, the spiraled cutting blades 42 operate to move ablated material proximally when the burr is rotated in the proper direction. Preferably, the spirals are oriented such that the ablated material is moved proximally when the more aggressive cutting blades are used to remove deposits because the more aggressive cutting blades will tend to remove larger pieces of occluding matter. In addition to the action of the spiraled blade, aspiration may also be applied to the surrounding catheter.

As will be appreciated, the present invention provides a single atherectomy burr that can be used to ablate different types of deposits in a vessel. For example, the less aggressive cutting blades can be used to remove harder scar tissue that forms at an anastomosis at the entrance of an SVG. Once the burr has passed into the SVG, the burr can be rotated to utilize the more aggressive cutting blades in order to -cut through the fibrous cap that covers a lesion. Thereafter, cutting can continue with the more aggressive cutting blades to remove the underlying occluding matter within the vessel. As the occluding matter is being removed, aspiration can be applied to the catheter to prevent the ablated particles from flowing distally within the vessel.

As can be seen by selectively operating the burr in either direction, the cutting rate and/or cutting characteristics of the burr can be selected by the physician in order to use a single burr to ablate a greater number of tissue types.

The burr may also be designed to provide no ablation in one direction of rotation and ablation in the other direction. The non-ablating direction of rotation would be engaged while the physician accesses the treatment site. It is easier to move the burr past an anastomosis or tortuous section while the burr is spinning due to the orthogonal displacement of friction. This burr could be shaped like the burrs in FIGS. 1 and 2 or FIGS. 3 and 4, but have no abrasive coating on the outer surface.

While the preferred embodiment of the invention has been illustrated and described, it will be appreciated that various changes can be made therein without departing from the scope of the invention. The scope of the invention is therefore to be determined from the following claims and equivalents thereto.

The embodiments of the invention in which an exclusive property or privilege is claimed are defined as follows:

1. A bi-directional atherectomy device for removing deposits from a vessel comprising:
    a driveshaft coupled to a source of bi-directional rotational motion;
    a burr body coupled to the driveshaft, the burr body including one or more stepped blades extending along at least a portion of a length of the burr body, the stepped blades having a first edge covered with an abrasive that is generally parallel to the outer surface of the burr body and a second edge that is free of abrasive and substantially perpendicular to the outer surface of the burr body,
    wherein the first edge of the one or more stepped blades removes deposits from a vessel with a first cutting action when the burr is rotated in a first direction and the second edge of the one or more stepped blades removes deposits with a more aggressive cutting action when rotated in a second direction.

2. The bi-directional atherectomy device of claim 1, wherein the one or more stepped blades are spiraled along at least a portion of a length of the burr body.

3. The bi-directional atherectomy device of claim 1, wherein the one or more stepped blades extend from a distal end of the burr body to a proximal end of the burr body.

4. An atherectomy device for removing deposits from a vessel comprising:
    a source of bi-directional rotation;
    a driveshaft coupled to the source of bi-directional rotation;
    an atherectomy burr coupled to the driveshaft, the burr having a number of blades having a cutting action when rotated in a first direction and a more aggressive cutting action when rotated in a second direction.

5. The atherectomy device of claim 4, wherein the number of blades have an abrasive surface that removes deposits from a vessel when the burr is rotated in the first direction and a cutting surface that removes deposits from a vessel when the burr is rotated in the second direction.

6. The atherectomy device of claim 4, wherein the abrasive surface of the cutting blades is generally parallel to the outer surface of the burr body and the cutting surface of the number of blades is generally perpendicular to the outer surface of the burr body.

7. The atherectomy device of claim 4, wherein the burr has an ablative action when rotating in one direction and no ablative action when rotating in the second direction.

8. A method of removing deposits from a vessel, comprising:
    advancing an atherectomy device into a vessel, the atherectomy device including:
        a source of bi-directional rotational motion;
        a driveshaft coupled to the source of bi-directional motion;
        a burr coupled to the driveshaft, the burr having a less aggressive cutting action when rotated in a first direction and a more aggressive cutting action when rotated in a second direction;
    selectively rotating the burr in the first and second direction to remove deposits from the vessel.

9. The method of claim 7, further comprising aspirating the vessel to remove ablated debris when the burr is rotated in the second direction.

* * * * *

UNITED STATES PATENT AND TRADEMARK OFFICE
CERTIFICATE OF CORRECTION

PATENT NO. : 6,503,261 B1
DATED : January 7, 2003
INVENTOR(S) : R.J. Bruneau et al.

It is certified that error appears in the above-identified patent and that said Letters Patent is hereby corrected as shown below:

Column 4,
Line 55, "claim 7," should read -- claim 8, --

Signed and Sealed this

Twenty-sixth Day of October, 2004

JON W. DUDAS
*Director of the United States Patent and Trademark Office*